(12) United States Patent
Sano

(10) Patent No.: US 10,758,373 B2
(45) Date of Patent: Sep. 1, 2020

(54) BONE MATERIAL DELIVERY SYSTEM

(71) Applicant: Warsaw Orthopedic, Inc., Warsaw, IN (US)

(72) Inventor: Takahiro Sano, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 229 days.

(21) Appl. No.: 15/866,728

(22) Filed: Jan. 10, 2018

(65) Prior Publication Data
US 2019/0209340 A1    Jul. 11, 2019

(51) Int. Cl.
*A61F 2/46*   (2006.01)
*A61B 17/88*  (2006.01)
*A61B 17/34*  (2006.01)

(52) U.S. Cl.
CPC ........ *A61F 2/4601* (2013.01); *A61B 17/3472* (2013.01); *A61B 17/8805* (2013.01)

(58) Field of Classification Search
CPC . A61B 17/3472; A61B 17/88; A61B 17/8802; A61B 17/8805; A61B 17/8811; A61B 17/8816; A61B 17/8819; A61B 17/8822; A61B 17/8825; A61F 2/4601
See application file for complete search history.

(56) References Cited

U.S. PATENT DOCUMENTS

| | | | |
|---|---|---|---|
| 4,820,287 A * | 4/1989 | Leonard | A61M 5/31581 604/135 |
| 6,045,555 A | 4/2000 | Smith et al. | |
| 6,174,311 B1 * | 1/2001 | Branch | A61B 17/1671 606/60 |
| 6,582,438 B2 | 6/2003 | DeMayo | |
| 7,008,433 B2 | 3/2006 | Voellmicke et al. | |
| 7,316,689 B2 * | 1/2008 | Lieberman | A61B 17/00234 606/93 |
| 7,972,340 B2 | 7/2011 | Sand et al. | |
| 8,034,088 B2 | 10/2011 | Pagano | |

(Continued)

FOREIGN PATENT DOCUMENTS

| | | |
|---|---|---|
| EP | 2774583 B1 | 11/2015 |
| WO | 2013119445 A1 | 8/2013 |

OTHER PUBLICATIONS

International Search Report and Written Opinion for PCT/US2019/012465, the counterpart application, dated May 1, 2019, 12 pages.

*Primary Examiner* — Eric S Gibson
(74) *Attorney, Agent, or Firm* — Sorell, Lenna & Schmidt, LLP

(57) ABSTRACT

A device for delivering a bone material to a surgical site is provided. The device comprises a body having an upper portion and a lower portion. The lower portion of the body is substantially transverse to the upper portion and has an opening for receiving a bone material. An internal chamber is disposed within the upper portion and the lower portion, and a plunger is slidably disposed in at least the internal chamber of the body. The plunger has a distal end configured for delivering the bone material out of the lower portion of the body, wherein movement of the plunger in a first position toward the lower portion of the body delivers the bone material from the lower portion of the body to the surgical site. Methods of delivering the bone material are also provided.

19 Claims, 8 Drawing Sheets

(56) References Cited

U.S. PATENT DOCUMENTS

| | | | |
|---|---|---|---|
| 9,033,994 B2* | 5/2015 | Fingerhut | A61F 2/4601 |
| | | | 606/100 |
| 9,247,943 B1* | 2/2016 | Kleiner | A61B 17/1659 |
| 9,629,729 B2* | 4/2017 | Grimberg, Jr. | A61F 2/4601 |
| 10,195,053 B2* | 2/2019 | Kleiner | A61F 2/4455 |
| 2003/0236573 A1* | 12/2003 | Evans | A61L 27/12 |
| | | | 623/23.58 |
| 2004/0215201 A1* | 10/2004 | Lieberman | A61B 17/00234 |
| | | | 606/93 |
| 2010/0179507 A1* | 7/2010 | Hess | A61B 17/8833 |
| | | | 604/500 |
| 2013/0131683 A1* | 5/2013 | Shah | A61B 17/8802 |
| | | | 606/93 |
| 2013/0190718 A1* | 7/2013 | Fingerhut | A61B 17/8805 |
| | | | 604/506 |
| 2013/0226188 A1 | 8/2013 | Campion et al. | |
| 2015/0045799 A1* | 2/2015 | Budyansky | A61F 2/4644 |
| | | | 606/84 |
| 2015/0112352 A1 | 4/2015 | Krause et al. | |
| 2016/0106551 A1* | 4/2016 | Grimberg, Jr. | A61F 2/4601 |
| | | | 623/17.16 |
| 2016/0296344 A1 | 10/2016 | Greenhalgh et al. | |
| 2017/0224397 A1* | 8/2017 | Grimberg | A61F 2/4455 |
| 2017/0238984 A1* | 8/2017 | Kleiner | A61F 2/4611 |
| 2017/0266342 A1* | 9/2017 | Evans | A61L 27/24 |
| 2019/0209340 A1* | 7/2019 | Sano | A61B 17/3472 |

* cited by examiner

ND DELIVERY SYSTEM

BONE MATERIAL DELIVERY SYSTEM

BACKGROUND

The use of bone material (e.g., bone graft, demineralized bone matrix, bone substitute material, etc.) in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture, Unlike bone, which can heal small damaged cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with bone material. Over time, the bone material is incorporated by the host and new bone remodels the bone material. In order to implant the bone material, it is common to use a bone material delivery tool.

Currently, there are various delivery tools used for bone material delivery, however, not many tools can be used effectively when performing minimally invasive percutaneous spinal procedures. Percutaneous spinal procedures involve access to the spine via needle-puncture of the skin, rather than by using an open approach where the spine is exposed. Because of the limited amount of access to the spine, there can be challenges when delivering bone material percutaneously during minimally invasive surgical procedures. For example, it can be challenging to place bone material percutaneously since the small incisions made in a patient do not provide enough room for surgeons to directly access the surgical site. Further, often the location of the surgical site, for example, at the spine can be a difficult location to implant bone material as the location may be very close to a nerve.

Therefore, it would be beneficial to provide devices for effectively delivering bone material (e.g., bone graft, demineralized bone matrix, bone substitute material, etc.) percutaneously to a target tissue site. Methods of delivering bone material and kits to allow delivery of the bone material would also be beneficial.

SUMMARY

Devices and methods are provided for delivering a bone material to a surgical site. In one embodiment, a device for delivering a bone material to a surgical site is provided. The device comprises a body having an upper portion and a lower portion. The lower portion of the body is substantially transverse to the upper portion and has an opening for receiving a bone material. An internal chamber is disposed within the upper portion and the lower portion, and a plunger is slidably disposed in at least the internal chamber of the body. The plunger has a distal end configured for delivering the bone material out of the lower portion of the body, wherein movement of the plunger in a first position toward the lower portion of the body delivers the bone material from the lower portion of the body to the surgical site.

In some embodiments, a device for delivering a bone material to a surgical site is provided. The device comprises a sleeve having an upper portion and a lower portion. The lower portion of the sleeve is substantially transverse to the upper portion and has a compartment for receiving a bone material. An internal chamber is disposed within the upper portion and the lower portion of the sleeve, and a plunger is slidably disposed in at least the internal chamber of the sleeve. The plunger has a distal end comprising a plate configured for delivery of the bone material. Movement of the plunger in a first position toward the lower portion of the sleeve delivers the bone material out of the lower portion of the sleeve to the surgical site.

In some embodiments, a method of delivering a bone material to a surgical site is provided, the method comprising: providing a bone material delivery device comprising a sleeve having an upper portion and a lower portion, the lower portion of the sleeve being substantially transverse to the upper portion and having a compartment for receiving a bone material, and an internal chamber disposed within the upper portion and the lower portion of the sleeve; and a plunger slidably disposed in at least the internal chamber of the sleeve, the plunger having a proximal end comprising a lever and a distal end comprising a plate; loading the compartment of the bone material delivery device with the bone material; and moving the plunger in a first position toward the lower portion of the sleeve to deliver the bone material out of the lower portion of the sleeve and into the surgical site.

In some embodiments, the bone material is percutaneously delivered to the surgical site or the surgical site is the posterior spine.

While multiple embodiments are disclosed, still other embodiments of the present application will become apparent to those skilled in the art from the following detailed description, which is to be read in connection with the accompanying figures. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

The present disclosure will become more readily apparent from the specific description accompanied by the following figures.

Figure 1:
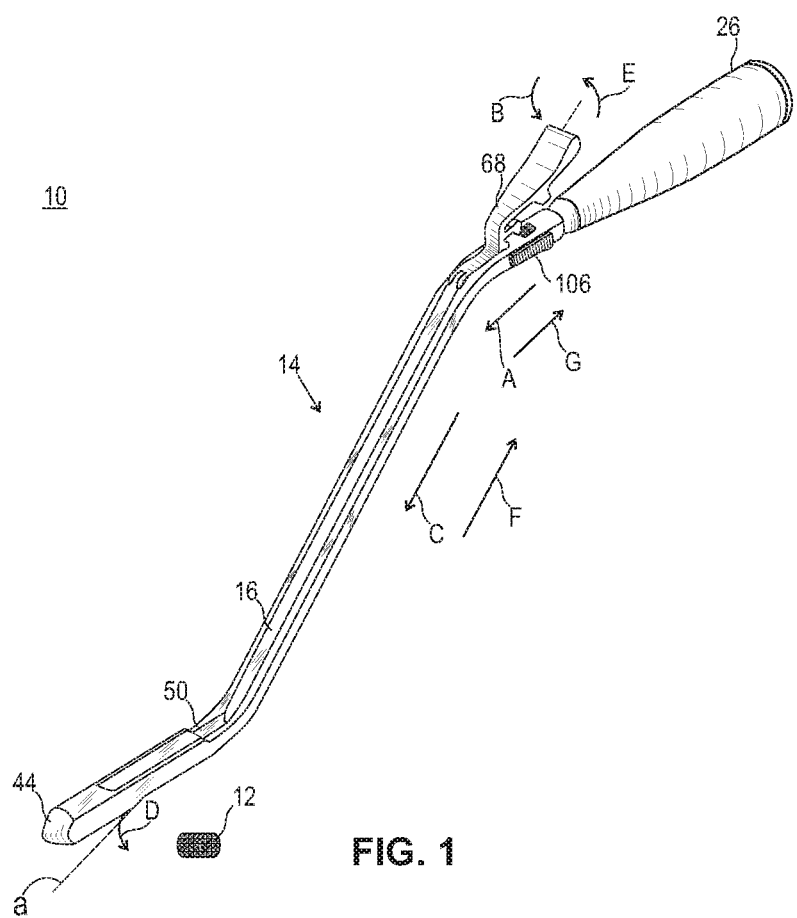
FIG. 1 is a perspective view of one embodiment of a device for delivering bone material to a surgical site. The device percutaneously delivers a bone material (e.g., bone graft, demineralized bone matrix, bone substitute material, etc.) to a surgical site. The device comprises a body, such as, a sleeve. The sleeve is configured for engagement with a plunger and the bone material, such that when the plunger is moved in a first position, the bone implant is deployed from the sleeve and into the surgical site.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

The bone material can have a bioactive agent or bioactive compound. Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in *Pharmaceutical Substances: Syntheses, Patents, Applications* by Axel Kleemann and Jurgen Engel, Thieme Medical Publishing, 1999; Merck Index: *An Encyclopedia of Chemicals, Drugs, and Biologicals*, edited by Susan Budavari et al., CRC Press, 1996; and *United States Pharmacopoeia-25/National Formulary-20*, published by the United States Pharmacopoeia Convention, Inc., Rockville Md., 2001, each of which is incorporated herein by reference.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

Bone material refers to material intended to be implanted into a bone defect and includes natural bone material, synthetic bone material, polymers and/or combinations thereof.

Demineralized, as used herein, refers to any material generated by removing mineral material from tissue, for example, bone tissue. In certain embodiments, demineralized bone material may be added to the bone void filler. The demineralized bone material described herein include preparations containing less than 5%, 4%, 3%, 2% or 1% calcium by weight. Partially demineralized bone (for example, preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," "superficially demineralized," and "fully demineralized." in some embodiments, part or all of the surface of the bone can be demineralized. For example, part or all of the surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the bone material can comprise demineralized material.

Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (for example, preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," *Clinical Orthopaedics & Rel. Res.*, 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance, the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are demineralized, however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. The non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular."

The term "bone fastener" or "bone fasteners" refer to multi-axial screws, uni-axial screws, fixed axis screws, sagittal adjusting screws, transverse sagittal adjusting screws, pedicle screws, uni-planar screws, facet screws, tissue penetrating screws, conventional screws, expanding screws and/or posts.

Percutaneous, as used herein, refers to a surgical method where entry to the spine is by puncture or minor incision, of instrumentation through the skin or mucous membrane and/or any other body layers necessary to reach the site of the procedure.

The devices, bone materials, kits and methods may be employed to treat spinal disorders such as, for example, degenerative disc disease, disc herniation, osteoporosis, spondylolisthesis, stenosis, scoliosis and other curvature abnormalities, kyphosis, tumor and fractures. The devices, bone materials, kits and methods may be employed with other osteal and bone related applications, including those associated with diagnostics and therapeutics. They may also be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The devices, bone materials, kits and methods may also be alternatively employed with procedures for treating the lumbar, cervical, thoracic, sacral and pelvic regions of a spinal column. They may also be used on animals, bone models and other non-living substrates, such as, for example, in training, testing and demonstration.

In various embodiments, the bone material comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the devices, bone materials, kits and methods are used in minimally invasive surgeries and the bone material is percutaneously delivered to a surgical site or the surgical site is the posterior spine.

In one embodiment, a delivery system is provided that allows surgeons to load bone material (e.g., bone graft) into a bone material chamber of a device, percutaneously insert the device toward a target location through small incisions and deploy the bone material into the target locations. The delivery system can be used to work with existing bone material options for grafting such as Magnifuse®, available from Medtronic, Inc. and other products. In one embodiment, a device is provided that comprises a chamber to securely load and store bone material while it is being delivered to a target location, a plunger used to deploy and position the loaded bone material at the target location, and a lever and button to manipulate the plunger.

Devices for Delivering Bone Material

Figure 2:
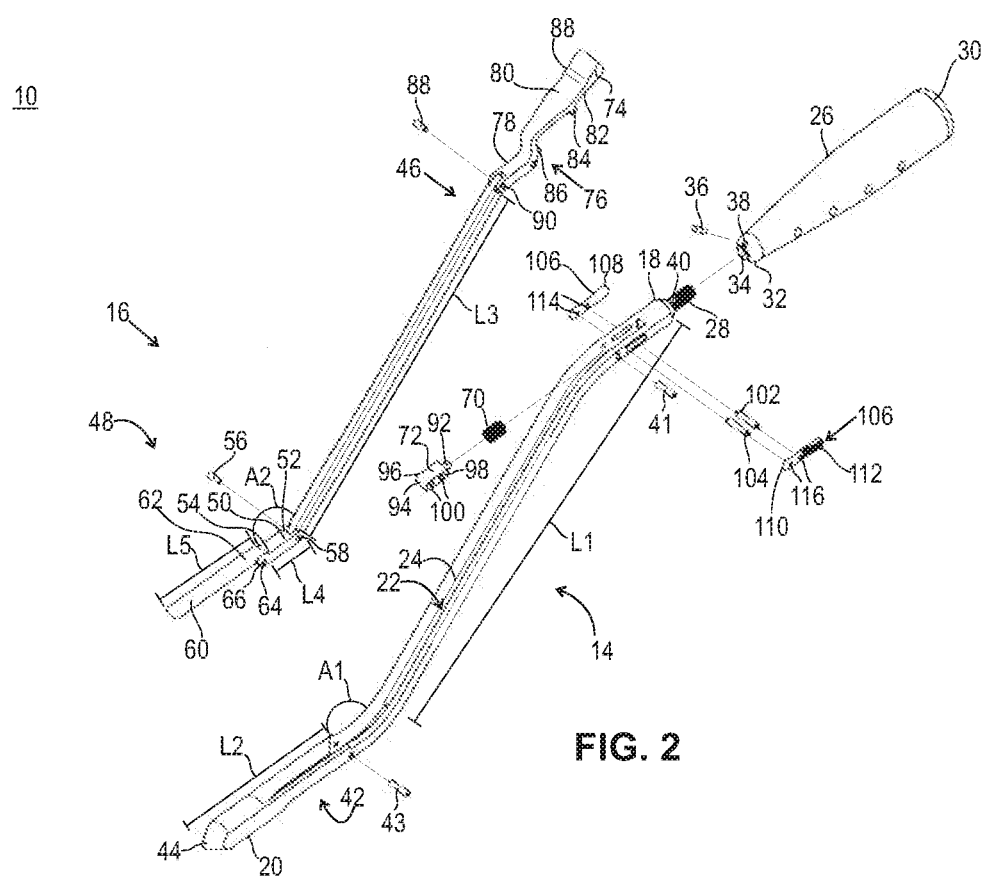
FIG. 2 is an exploded view of components of device of FIG. 1.
Figure 3:
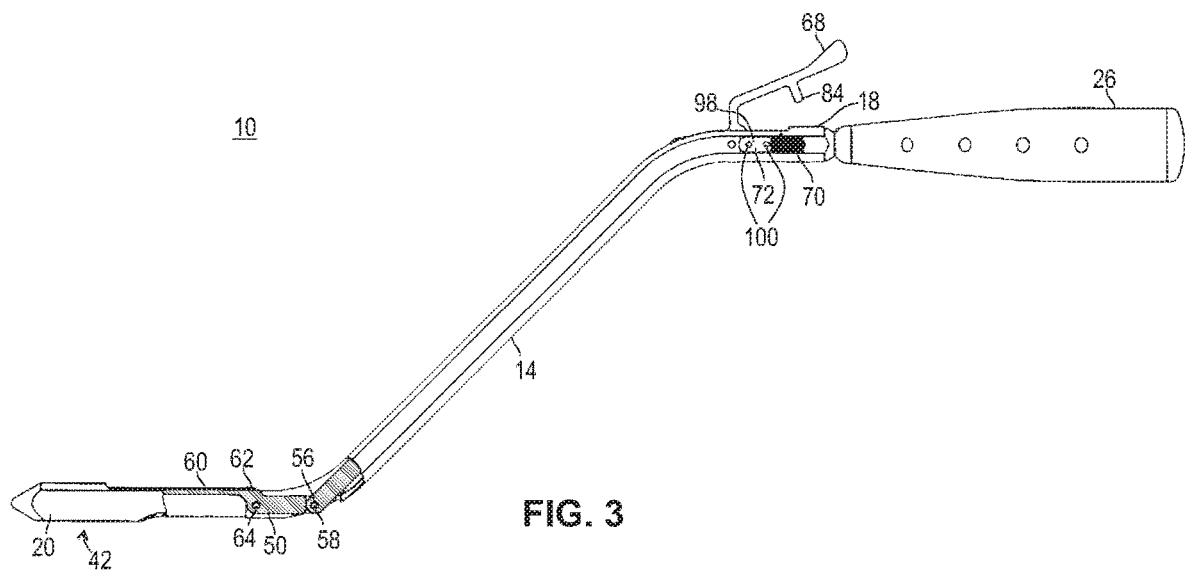
FIG. 3 is a side cross-sectional view of the device of FIG. 1.

Referring to FIGS. 1 to 3, a device 10 is provided for percutaneously delivering a bone material (e.g., a biodegradable mesh with bone material disposed within the mesh) 12 to a surgical site. The device comprises a body, such as a sleeve 14. The sleeve is configured for engagement with a plunger 16 and the bone material, such that when the plunger is moved in a first position, the bone material is deployed from the sleeve and into the surgical site.

The sleeve includes an upper portion 18, and a lower portion 20. The lower portion of the sleeve is substantially transverse to the upper portion of the sleeve. In some embodiments, the lower portion of the sleeve is at an angle A1 relative to the upper portion. In some embodiments, angle A1 is from about 25 to about 90 degrees, from about 45 to about 90 degrees, or from about 25 to about 45 degrees relative to the proximal end. In some embodiments, angle A1 is from about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees relative to the upper portion.

The sleeve comprises an internal chamber 22 that is disposed within both the upper and lower portions. The internal chamber is configured for sliding engagement with the plunger, as described herein. An exterior surface of the sleeve defines an opening 24 that extends from the upper portion to the lower portion of the sleeve, and is configured to facilitate insertion of the plunger into the internal chamber. The length of the opening is less than the entire length of the sleeve. The opening may be rectangular shaped.

The upper portion of the sleeve comprises a handle 26 at an end 28. The handle includes a proximal end 30 and a distal end 32. The distal end of the handle defines a recess 34 configured for engagement with end 28. An interior surface of the recess and an exterior surface of the end can be smooth or threaded depending on the desired engagement. The recess of the handle slides over end 28 and is fixedly connected via a fastening element, such as a screw 36. The screw is inserted into an opening 38 located on the distal end of the handle and is then inserted into an opening 40 that is located on end 28.

The lower portion of the sleeve defines an opening, such as a compartment 42 and an end 44. The compartment is configured for receiving a bone material. The compartment is adjacent end 44 and is on an opposing side relative to opening 24. The compartment can be any size or dimension depending on the size of the bone material (e.g., bone graft) that is to be placed at the surgical site. The compartment is configured to be large enough to hold the bone material in place until delivery is desired. A user loads the bone material into the compartment prior to the procedure. As described above, the lower portion of the sleeve includes end 44 that is tapered. In some embodiments, the end may be blunt or hooked, depending on the desired application of the device.

The upper portion of the sleeve has a length L1 and the lower portion of the sleeve has a length L2. Length L1 has a length that is greater than length L2. In some embodiments, length L1 is less than length L2, or length L1 and length L2 are the same length. In some embodiments, the length of L1 and/or L2 is from about 15 to 200 millimeters (mm), from about 50 to about 100 mm, from about 60 to 80 mm, or from about 70 to 75 mm. In some embodiments, the length of L1 and/or L2 is from about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mm. Pins 41 and 43 are used to stabilize the sleeve and the plunger as shown in FIG. 2.

The device includes a plunger 16, as described above that is slidably disposed in at least the internal chamber of the sleeve. The plunger includes a proximal end 46, a distal end 48, and longitudinal axis a is disposed between the ends. The distal end of the plunger is substantially transverse to the proximal end of the plunger. In some embodiments, the distal end of the plunger is at an angle A2 relative to the proximal end. In some embodiments, angle A2 is from about 25 to about 90 degrees, from about 45 to about 90 degrees, or from about 25 to about 45 degrees relative to the proximal end. In some embodiments, angle A2 is from about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees relative to the proximal end.

The distal end of the plunger is configured for delivering the bone material out of the compartment located in the lower portion of the sleeve. Movement of the plunger in a first position by a lever, as described herein, toward the lower portion of the sleeve delivers the bone material from the lower portion of the sleeve into the surgical site.

The distal end of the plunger comprises a link 50 pivotably attached to a plate 60. The link includes a first end 52 and a second end 54. The first end of the link is attached to an end of the proximal end of the plunger via a fastening member, such as a pin 56 that is inserted into a hole 58 formed within the end of the proximal end of the plunger. The second end of the link is attached to a proximal end 62 of the plate via a fastening member, such as a pin 64 that is inserted into a hole 66 formed within the second end of the link. The plate is configured for engagement with the bone material, and when the plunger is moved in the first position, the plate is pivoted by the link in a downward direction to eject the bone material from the plate, out of the compartment of the lower portion of the sleeve, and into the surgical site.

The proximal end of the plunger has a length L3, the link has a length L4 and the plate has a length L5. Length L3 is greater than both L4 and L5. In some embodiments, length L4 is less than length L5. In some embodiments, length L4 is the same as length L5 or the length of L4 is greater than length L5. In some embodiments, length L3 is from about 10 mm to 175 mm, from about 15 mm to about 150 mm, from about 50 mm to about 100 mm, or from about 60 mm to about 80 mm. In some embodiments, length L3 is from about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, or 175 mm.

In some embodiments, length L4 and/or L5 is from about 10 mm to about 50 mm, from about 15 mm to about 40 mm, from about 20 to about 30 mm, from about 15 to about 20 mm, or from about 25 mm to about 35 mm. In some embodiments, length L4 and/or length L5 is from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mm.

The proximal end of the plunger comprises a lever 68 that engages with a spring 70 and a locking mechanism 72 to actuate movement of the plunger. The lever includes a first portion 74, a second portion 76 and a third portion 78. The first portion of the lever defines a top surface 80 and a bottom surface 82. The top surface is configured for engagement with a user's thumb and the bottom surface comprises a protuberance 84 that is configured for engagement with a portion of the upper portion of the sleeve. The second portion of the lever includes a lip 86 configured for engagement with an end of the locking mechanism, as described below. The third portion of the lever is fixed to an end of the proximal end of the plunger via a fastening member, such as a pin 88 that is inserted into a hole 90 formed within the end of the proximal end of the plunger.

The spring is disposed within the internal chamber adjacent end 28 of the sleeve. The locking member is then inserted within the internal chamber adjacent end 28 of the sleeve and behind the spring. The locking member has a first end 92 and a second end 94. The first end of the locking member is cylindrical and engages with the spring, and the second end of the locking member engages the lip of the second portion of the lever. The locking member further includes a left side 96 and a right side 98. A set of channels 100 run perpendicular and through the left and right sides of the locking member. The set of channels are configured for engagement with pins 102 and 104.

The plunger is disposed within the internal chamber of the sleeve and the proximal end of the plunger is disposed adjacent end 28 of the sleeve. The first portion of the lever is located outside of the internal chamber. A knob, such as, for example, a lock knob 106 includes a first bracket 108, and second bracket 110 comprising a button 112. Both the first bracket and the second bracket define a set of channels 114 and 116 that are configured for engagement with pins 102 and 104. Each of the brackets are mounted to opposing exterior surfaces of the upper portion of the sleeve adjacent end 28. The lock knob is configured to lock and release the lever, spring and locking mechanism to actuate movement of the plunger. For example, when the button of the lock knob is translated in a forward direction, as shown by arrow A in FIG. 1, and the lever is translated in a downward direction toward the handle, as shown by arrow B, the spring engages with the locking mechanism, the locking mechanism then engages with the lip of the second portion of the lever and the plunger is moved in a first position, as shown by arrow C. When the plunger is moved in the first position, the plate is pivoted by the link in a downward direction, as shown by arrow D, and the compartment located in the lower portion of the sleeve is opened, thereby ejecting a bone material (e.g., bone graft) out of the compartment and into a surgical site. Once the bone material is ejected, the lever is translated in an upward direction, away from the handle, as shown by arrow E, the plunger is moved in a second position, as shown by arrow F, the compartment closes and the button of the lock knob is translated in a backward direction, as shown by arrow G to lock the plunger.

Figure 4:
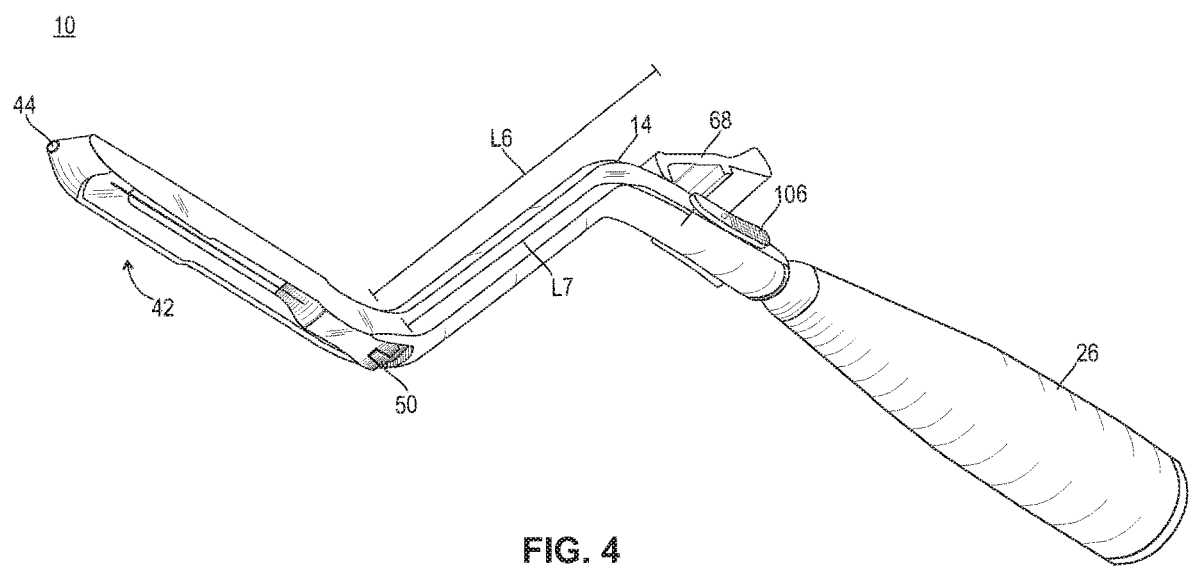
FIG. 4 is a perspective view of one embodiment of a device, similar to the device of FIG. 1 for delivering bone material to a surgical site. In this embodiment, the length of an upper portion of the sleeve and a proximal end of the plunger has been shortened relative to the length of an upper portion of the sleeve and a proximal end of the plunger as shown in FIG. 1.
Figure 5:
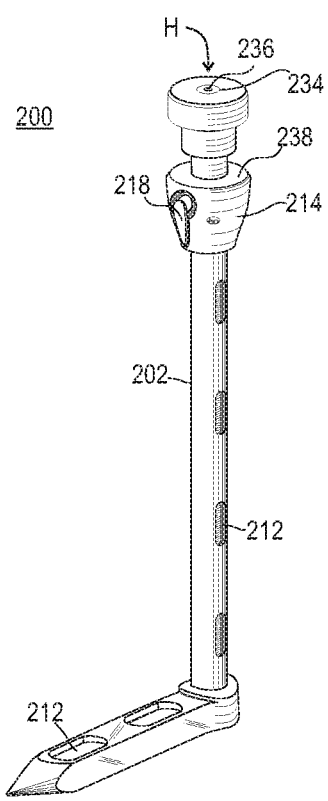
FIG. 5 is a perspective view of one embodiment of a device in an upright position for delivering bone material to a surgical site. The device, similar to the device shown in FIG. 1, is for percutaneous delivery of bone material (e.g., bone graft) to a surgical site. The device comprises a body, such as, a sleeve. The sleeve is configured for engagement with a plunger and the bone material, such that when the plunger is moved in a first position, the bone implant is deployed from the sleeve and into the surgical site.
Figure 6:
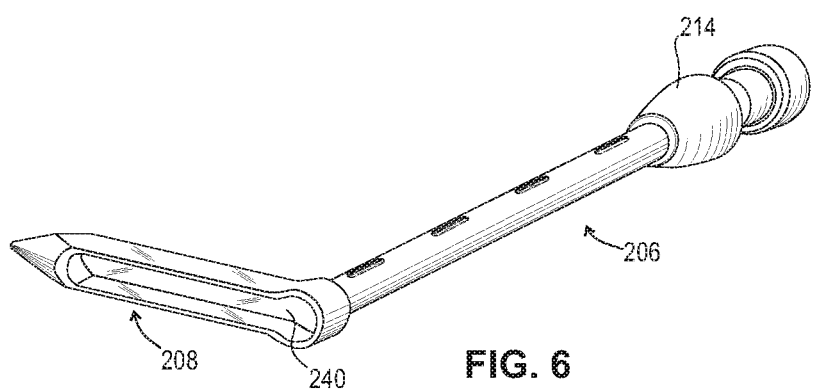
FIG. 6 is a perspective view of the device of FIG. 5 in a position.
Figure 7:
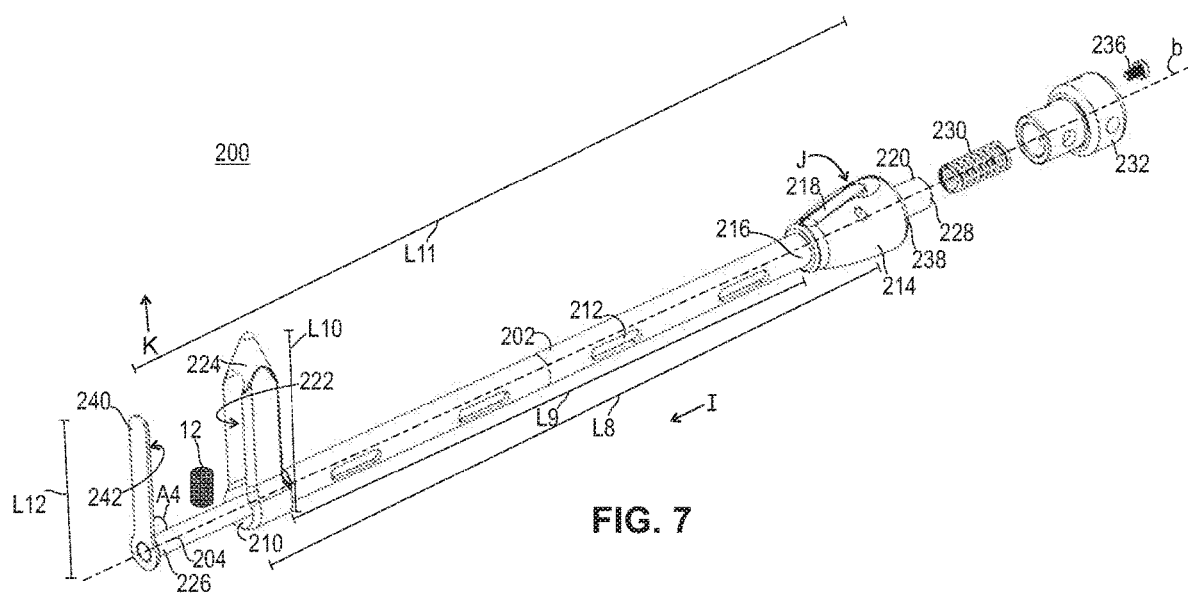
FIG. 7 is a perspective view of the device of FIG. 5, where the device is in a first position.
Figure 8:
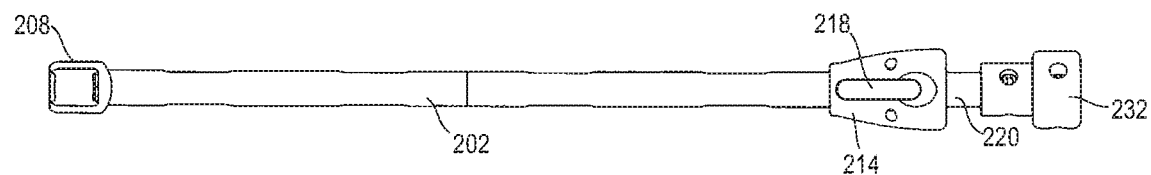
FIG. 8 is a top view of the device of FIG. 5.
Figure 9:
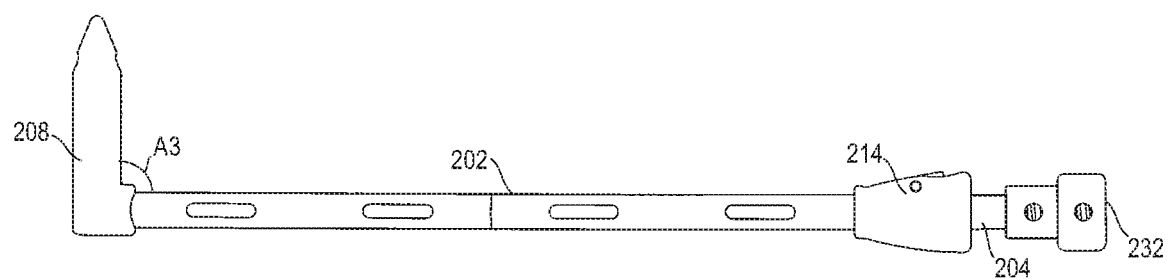
FIG. 9 is a side view of the device of FIG. 5.

In some embodiments, as shown in FIG. 4, at least the upper portion of the sleeve of device 10 has a different length L6 than length L1 depicted in FIG. 2. The proximal end of the plunger also has a different length L7 than length L3. In some embodiments, the length of the upper portion of the sleeve is the same length as the lower portion of the sleeve. In some embodiments, the length of the lower portion of the sleeve is greater than the length of the upper portion of the sleeve. In some embodiments, the length of the proximal end of the plunger is equal to the distal end of the plunger. In some embodiments, the length of the distal end of the plunger is greater than the length of the proximal end of the plunger. In some embodiments, the length of L6 and/or L7 is from about 10 to 200 millimeters (mm), from about 30 to about 100 mm, from about 50 to 80 mm, or from about 65 to 75 mm. In some embodiments, length L6 and/or L7 is from about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mm.

Referring to FIGS. 5 to 9, a device 200 is provided, similar to device 10, as described above, for percutaneously delivering bone material (e.g., bone graft) 12 to a surgical site. The device comprises a body, such as a sleeve 202. The sleeve is configured for engagement with a plunger 204 and the bone material, such that when the plunger is moved in a first position, the bone material (e.g., bone implant, bone material in a biodegradable mesh, demineralized bone, etc.) is deployed from the sleeve and into the surgical site.

The sleeve includes an upper portion 206, a lower portion 208 and a longitudinal axis b is disposed between the portions. The lower portion of the sleeve is substantially transverse to the upper portion of the sleeve. In some embodiments, the lower portion of the sleeve is at an angle A3 relative to the upper portion. In some embodiments, angle A3 is from about 25 to about 90 degrees, from about 45 to about 90 degrees, or from about 25 to about 45 degrees relative to the proximal end. In some embodiments, angle A3 is from about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees relative to the upper portion.

The sleeve comprises an internal chamber 210 that is disposed within both the upper and lower portions. The internal chamber is configured for sliding engagement with the plunger, as described herein. One or more windows 212 are formed from an exterior surface of the sleeve and extend along the entire length L8 of the sleeve. In some embodiments, the length of L8 is from about 15 to 240 millimeters (mm), from about 50 to about 150 mm, from about 60 to 100 mm, or from about 80 to 90 mm. In some embodiments, the length of L8 is from about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235 or 240 mm.

A lever housing 214 is fixed to an end 216 of the upper portion of the sleeve. The lever housing contains a lever 218. The lever housing engages with a proximal end 220 of the plunger and is configured to lock and unlock the sleeve and plunger for deployment of the bone graft.

The lower portion of the sleeve defines an opening, e.g., a compartment 222 and an end 224. The compartment is configured for receiving the bone material, and a user loads the bone material into the compartment prior to the procedure. The compartment can be any size or dimension depending on the size of the bone material (e.g., bone graft) that is to be placed at the surgical site. The compartment is configured to be large enough to hold the bone material in place until delivery is desired. As described above, the lower portion of the sleeve includes end 224 that is tapered. In some embodiments, the end may be blunt or hooked, depending on the desired application of the device.

The upper portion of the sleeve has a length L9 and the lower portion of the sleeve has a length L10. Length L9 has a length that is greater than length L10. In some embodiments, length L9 is less than length L10, or length L9 and length L10 are the same length. In some embodiments, the length of L9 and/or L10 is from about 15 to 200 millimeters (mm), from about 50 to about 100 mm, from about 60 to 80 mm, or from about 70 to 75 mm. In some embodiments, the length of L9 and/or L10 is from about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mm.

The device includes a plunger 204, as described above that is slidably disposed in at least the internal chamber of the sleeve. The plunger includes a proximal end 220, a distal end 226, and a longitudinal axis b is disposed between the ends. The distal end of the plunger is substantially transverse to the proximal end of the plunger. In some embodiments, the distal end of the plunger is at an angle A4 relative to the proximal end. In some embodiments, angle A4 is from about 25 to about 90 degrees, from about 45 to about 90 degrees, or from about 25 to about 45 degrees relative to the proximal end. In some embodiments, angle A4 is from about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees relative to the proximal end.

A first end 228 of the proximal end of the plunger engages a spring 230. The spring is encased in a housing 232 that defines an opening 234 that is configured for disposal of a fastening member, such as for example, cap screw 236. The screw is configured for engagement with a first portion of the spring, and a second portion of the spring contacts a top 238 of the lever casing such that when the housing is moved in a downward direction, as shown by arrow H in FIG. 5, the plunger is moved in a first position, as shown by arrow I in FIG. 7, and the lever casing locks and unlocks the housing by pushing the lever in an downward direction, as shown by arrow J.

The distal end of the plunger is configured for delivering the bone material out of the compartment located in the lower portion of the sleeve. Movement of the plunger in the first position, as described herein, toward the lower portion of the sleeve delivers the bone material from the lower portion of the sleeve into the surgical site.

The distal end of the plunger comprises a plate 240. The plate is oriented transverse relative to the sleeve. The plate includes an upper surface 242 that is configured for engagement with the bone material (e.g., bone graft). The bone material is inserted and contained between the compartment of the lower portion of the sleeve and the upper surface of the plate, and when the plunger is moved in the first position as shown by arrow I, the bone material is ejected out of the opening, as shown by arrow K in FIG. 7, out of the lower portion of the sleeve, and into the surgical site. A gap is formed between the plate and end 224 releasing the bone material. In this way, the bone material can be precisely delivered. End 224 of the device is tapered and sized to be place between vertebrae to allow easier delivery of the bone material.

The proximal end of the plunger has a length L11 and the distal end of the plunger has a length L12. Length L11 is greater than length L12. In some embodiments, length L11 is less than length L12. In some embodiments, length L11 is the same as length L12. In some embodiments, length L11 and/or L12 is from about 10 mm to 260 mm, from about 15 mm to about 200 mm, from about 50 mm to about 150 mm, or from about 100 mm to about 125 mm. In some embodiments, length L11 and/or L12 is from about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255 or 260 mm.

In some embodiments, components of the device can be fabricated from biologically acceptable materials suitable for medical applications, including metals, synthetic polymers, ceramics and/or their composites. For example, the components of the device, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, or any combination thereof.

In some embodiments, components of the device can have a selected modulus of elasticity including from about $1\times-10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

The device can have an outer surface having a selected texture, including, but not limited to smooth or rough, and may be coated or otherwise treated with a compound. The bone material may include bone morphogenic proteins (BMPs), growth factors, antibiotics, angiogenesis promoting materials, bioactive agents or other actively releasing materials, as described herein.

Kit

In various embodiments, a kit is provided with the device. The kit may include additional parts along with the device combined together to be used with the bone material (e.g., bone graft) and dilators (e.g., wipes, needles, syringes, etc.). The kit may include the device in a first compartment. The second compartment may include the bone material, along with a mesh or a vial containing diluent and any other instruments needed for the localized implant delivery. A third compartment may include gloves, drapes, wound dressings and other procedural supplies for maintaining sterility of the implanting process, as well as an instruction booklet, which may include a chart that shows how to implant the bone material. A fourth compartment may include additional needles, fasteners, and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Bone Material

In various embodiments, the bone material that can be delivered by the device may be particulated such as, for example, in bone chips, powder and/or fiber form that is mineralized and/or demineralized (e.g., fully demineralized, surface demineralized, etc.). If the bone is demineralized, the bone may be made into a particulate before, during or after demineralization. In some embodiments, the bone may be monolithic and may not be a particulate.

The bone may be milled and ground or otherwise processed into particles of an appropriate size before or after demineralization. The particles may be particulate (for example, powder) or fibrous. The terms milling or grinding are not intended to be limited to production of particles of a specific type and may refer to production of particulate or fibrous particles. In certain embodiments, the particle size may be greater than 25 microns, such as ranging from about 25 to about 2000 microns, or from about 25 to about 500 microns or from about 200 to about 1000 microns. In some embodiments, the size of the bone particles are less than 100 microns. In some embodiments, the size of the bone particles are less than 500 microns.

After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone material comprises DBM and/or mineralized bone. In some embodiments, the size of the bone material is less than 25 microns. In some embodiments, the bone material particle size is about 1, 2, 3, 4, 5, 6, 7, 8, 9, 10, 11, 12, 13, 14, 15, 16, 17, 18, 19, 20, 21, 22, 23, 24 and/or 25 microns.

In various embodiments, the bone powder, chips and/or the DBM and/or mineralized bone fibers have a sticky outer surface such that the bone material can adhere to DBM and/or mineralized bone fibers. In various embodiments, the bone powder is naturally sticky. In some embodiments, an adhesive agent is applied to the bone powder and/or the bone fibers comprising a bio-adhesive, glue, cement, cyanoacrylate, silicones, hot melt adhesives and/or cellulosic binders. In various embodiments, the adhesive may be applied to the surface of the bone powder by spraying or brushing. In some embodiments, a charge is applied to the fibers and an opposite charge is applied to the bone powder, (i.e., the technique of electrostatic precipitation). The bone powder will be attracted to, and tenaciously adhere to, the surface of the fiber. Any of these application techniques can be repeated one or more times to build up a relatively thick layer of adherent bone powder on the surface of the fibers.

The bone powder can be applied directly to the DBM fiber and/or fully mineralized fiber, chips and the mixture can be disposed in the mesh material and/or mesh body. In some embodiments, the bone material inserted into the mesh material and/or mesh body contains pores having a pore size from about 0.5 to about 2,000 microns. In some embodiments, bone material inserted into the mesh material and/or mesh body contains pores having a pore size of from about 0.5, 5, 50, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 to about 2,000 microns. In some embodiments, the pore size of the bone material is uniform. In some embodiments, the pore size of bone material is non-uniform and includes various pore sizes in the range from 0.5 to about 2,000 microns. Alternatively, the DBM fibers, chips, and DBM powder can be placed in a polymer (for example, collagen) and inserted into a porous biodegradable graft body (for example, a pouch, container, mesh material and/or mesh body, and the like).

Following shaving, milling or other technique whereby they are obtained, the bone material is subjected to demineralization in order to reduce its inorganic content to a very low level, in some embodiments, to not more than about 5% by weight of residual calcium and to not more than about 1% by weight of residual calcium. Demineralization of the bone material ordinarily results in its contraction to some extent.

The bone material can be loaded in the device by itself or it can have a carrier or binder with it or, in some embodiments, it can be disposed in a biodegradable mesh to be implanted.

Bone used in the methods described herein may be autograft, allograft, or xenograft. In various embodiments, the bone may be cortical bone, cancellous bone, or corticocancellous bone. While specific discussion is made herein to demineralized bone matrix, bone matrix treated in accordance with the teachings herein may be non-demineralized, demineralized, partially demineralized, or surface demineralized. This discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone material can be conducted in accordance with known conventional procedures. For example, in a preferred demineralization procedure, the bone materials useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone material is immersed in solution to effect its defatting. A defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The concentration range of the defatting solution is from about 60 to 85 weight percent alcohol or about 70 weight percent alcohol.

Further in accordance with this application, the DBM material can be used immediately for preparation of the bone implant or it can be stored under aseptic conditions, advantageously in a critical point dried state prior to such preparation. In one embodiment, the bone material can retain some of its original mineral content such that the composition is rendered capable of being imaged utilizing radiographic techniques.

In various embodiments, this application also provides bone matrix compositions comprising critical point drying (CPD) fibers. DBM includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-$\beta$, IGF, and BMP protein families. Particular examples of osteoinductive factors include TGF-$\beta$, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in this application can be prepared from elongated bone fibers which have been subjected to critical point drying (CPD). The elongated CPD bone fibers employed in this application are generally characterized as having relatively high average length to average width ratios, also known as the aspect ratio. In various embodiments, the aspect ratio of the elongated bone fibers is at least from about 50:1 to at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the chips to fibers ratio is about 90:10, 80:20, 75:25, 70:30, 60:40, 50:50, 40:60, 30:70, 25:75, 20:80 and/or 10:90. In various embodiments, a surface demineralized chips to fibers ratio is about 90:10, 80:20, 75:25, 70:30, 60:40, 50:50, 40:60, 30:70, 25:75, 20:80 and/or 10:90. In some embodiments, a surface demineralized chips to fully demineralized fibers ratio is about 90:10, 80:20, 75:25, 70:30, 60:40, 50:50, 40:60, 30:70, 25:75, 20:80 and/or 10:90.

In some embodiments, the DBM fibers have a thickness of about 0.5-4 mm. In various embodiments, the DBM fibers have a thickness of about 0.5, 0.6, 0.7, 0.8, 0.9, 1, 1.5, 2, 2.5, 3, 3.5 and/or 4 mm. In various embodiments, the ratio of DBM fibers to DBM powder is about 40:60 to about 90:10 W/W, W/V or V/V. In some embodiments, the ratio of mineralized bone fibers to DBM powder is about 25:75 to about 75:25 W/W, W/V or V/V. In various embodiments, the bone implant comprises DBM fibers and mineralized fibers in a ratio of 40:60 to about 90:10 W/W, W/V or V/V. In some embodiments, the DBM fibers to DBM powder ratio, mineralized bone fibers to DBM powder ratio and/or the DBM fibers and mineralized fibers ratio is from 5:95 to about 95:5 W/W, W/V or V/V. In some embodiments, the DBM fibers to DBM powder ratio, mineralized bone fibers to DBM powder ratio and/or the DBM fibers and mineralized fibers ratio is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 W/W, W/V or V/V.

In some embodiments, the bone material comprises demineralized bone material comprising demineralized bone, fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In various embodiments, the bone material comprises fully DBM fibers and surface demineralized bone chips. In some embodiments, the ratio of fully DBM fibers to surface demineralized bone chips is from 5:95 to about 95:5 fibers to chips. In some embodiments, the ratio of fully DBM fibers to surface demineralized bone chips is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 fibers to chips. In various embodiments, the fully DBM fibers have a thickness of about 0.5-4 mm. In various embodiments, the fully DBM fibers have a thickness of about 0.5, 0.6, 0.7, 0.8, 0.9, 1, 1.5, 2, 2.5, 3, 3.5 and/or 4 mm.

In various embodiments, the fibers and/or the powder is surface DBM. In some embodiments, the fibers and/or the powder is surface DBM cortical allograft. In various embodiments, surface demineralization involves surface demineralization to at least a certain depth. For example, the surface demineralization of the allograft can be from about 0.25 mm, 0.5 mm, 1 mm, 1.5 mm, 2.0 mm, 2.5 mm, 3.0 mm, 3.5 mm, 4 mm, 4.5 mm, to about 5 mm. The edges of the bone fibers and/or powder may further be machined into any shape or to include features such as grooves, protrusions, indentations, etc., to help improve fit and limit any movement or micromotion to help fusion and/or osteoinduction to occur.

To prepare the osteogenic DBM, a quantity of fibers is combined with a biocompatible carrier to provide a demineralized bone matrix.

DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using a critical point drying technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound by a particular theory, this deformation and structure is thought to occur because as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluorotmethane), may be used. Generally, fluids suitable for supercritical drying include carbon dioxide (critical point 304.25 K at 7.39 MPa or 31.1° C. at 1072 psi or 31.2° C. and 73.8 bar) and Freon (about 300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

Suitable bone material for delivery by the device include, for example, MAGNIFUSE® Bone Graft, MASTER-GRAFT® Matrix, and GRAFTON® DBM, all available from Medtronic, Inc.

Mesh Formulations

The bone material (e.g., bone graft) can be disposed in a mesh material and/or mesh body and may be configured from woven threads that are configured to allow ingrowth of cells while also retaining the bone material within the compartment of the bone implant. The threads of the mesh may have a predetermined thickness of about 0.01 mm to about 2.0 mm, about 0.05 mm to about 1.0 mm, or about 0.1 to about 0.5 mm. The thickness of the threads may be uniform along the length of each thread, or varied across the length of each thread. In some embodiments, some threads have a greater thickness than other threads. The threads may be sized to allow for customizable pore sizes between the threads. In some embodiments, the bone material (e.g., bone graft) is configured to facilitate transfer of substances and/or materials surrounding the surgical site. Upon implantation to a surgical site, the bone material may participate in, control, or otherwise adjust, or may allow penetration of the mesh by surrounding materials, such as cells or tissue.

The mesh may be sized according to the needs of a particular application. For example, the mesh may include dimensions between about 1 mm to about 100 mm in diameter. In some embodiments, the mesh includes a diameter of about 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm. In some embodiments, the mesh includes a length or depth between about 0.1 cm to about 10 cm. In some embodiments, the mesh includes a length or depth of about 1 cm, 2 cm, 3 cm, 4 cm, 5 cm, 6 cm, 7 cm, 8 cm, 9 cm, or 10 cm.

In some embodiments, the mesh can have selected dimensions, such as, for example, a diameter of 0.5 cm and a length of 0.1 cm, providing a volume of 0.02 cc. In other embodiments, the mesh can have a diameter of 1 cm and a length of 1 cm, providing a volume of 0.79 cc. In yet other embodiments, a mesh bag has a diameter of 1.5 cm and length of 3 cm, providing a volume of 5.3 cc.

The shape, mesh size, thickness, and other structural characteristics, of the mesh material and/or mesh body, for example, architecture, may be customized for the desired application. For example, to optimize cell or fluid migration through the mesh, the pore size may be optimized for the viscosity and surface tension of the fluid or the size of the cells. For example, pore sizes between threads on the order of approximately 100-200 μm may be used if cells are to migrate through the mesh. In other embodiments, wave-shaped threads may be extruded to have larger peaks and crests and the size of the pores may be larger. For example, in some embodiments, the pore size between threads may be about 0.1 mm to about 5 mm, about 0.5 mm to about 3 mm, or about 1 mm to about 2 mm. Mesh size may be controlled by physically weaving strands and by controlling the thickness of threads.

The mesh may have varying degrees of permeability across its surface. It may be permeable, semi-permeable, or non-permeable. Permeability may be with respect to cells, to liquids, to proteins, to growth factors, to bone morphogenetic proteins, or other. In further embodiments, the material may be braided.

The mesh material and/or mesh body may have any suitable configuration. For example, the mesh material and/or mesh body can have a variety of shapes, such as, for example, a ring, a cylinder, a cage, a rectangular shape, a suture-like wrap, a continuous tube, or other configurations. The mesh material and/or mesh body may be formed as a thin tube designed to be inserted through catheters or an introducer tube; a rectangular shape designed to fit adjacent to spinal processes for posterolateral spine fusion; a cube; a rectangular prism like structure designed to fit between vertebral bodies or within cages for interbody spinal fusion; a tube-like shape; relatively flat shapes; rectangular shapes; structures pre-shaped to fit around various implants (e.g., dental, doughnut with hole for dental implants); or relatively elastic ring-like structures that will stretch and then conform to shapes (e.g. rubber band fitted around processes).

Additionally, in some embodiments, the flexible character of the mesh allows for the mesh material and/or mesh body to be manipulated into a plurality of compartments. For example, in a tubular embodiment, the tube may be formed into a plurality of compartments by tying a cord around the tube at one or more points, or by other suitable mechanism such as crimping, twisting, knotting, stapling, or sewing.

An example of the mesh material and/or mesh body can be the MAGNIFUSE® Bone Graft, available from Medtronic, Inc. which comprises surface demineralized bone chips mixed with non-demineralized cortical bone fibers or fully demineralized bone fibers sealed in an absorbable poly(glycolic acid) (PGA) mesh implant or bag or pouch.

In certain embodiments, a bone void can be filled by mesh material and/or mesh body containing bone material. A compartment within mesh material and/or mesh body can be at least partially filled with a bone repair substance. In various embodiments, at least partially filled as used herein, can mean that a percentage of the volume of a compartment or hollow interior region is at least 70% occupied, at least 75% occupied, at least 80% occupied, at least 85% occupied, at least 90% occupied, at least 95% occupied, or 100% occupied. Mesh material and/or mesh body can be inserted into an opening in the defect until the defect is substantially filled. In various embodiments, substantially filled, as used herein, can mean that a percentage of the volume of a defect is at least 70% occupied, at least 75% occupied, at least 80% occupied, at least 85% occupied, at least 90% occupied, at least 95% occupied, or 100% occupied.

In some embodiments, mesh material and/or mesh body may be labeled. Such labeling may be done in any suitable manner and at any suitable location on the mesh material and/or mesh body. In some embodiments, labeling may be done by using a silk screen printing, using an altered weaving or knotting pattern, by using different colored threads, or other means. The labeling may indicate information regarding mesh material and/or mesh body. Such information might include a part number, donor ID number, number, lettering or wording indicating order of use in the procedure or implant size, etc.

The mesh material and/or mesh body may comprise a penetrable material at a first compartment configured for placement adjacent bone and a substantially impenetrable material at a second compartment configured for placement adjacent soft tissue. For example, the pore size between the threads at a first region of the mesh material and/or mesh body may be sized large enough to allow cell migration through the mesh material and/or mesh body, but the pore size between the threads at a second region of the mesh material and/or mesh body may be sized small enough (or may include a lack of pores altogether) to prevent cell migration. Alternatively, the material of the mesh material and/or mesh body may have a uniform configuration such that adjacent compartments may have substantially identical characteristics. By way of example only, the mesh material and/or mesh body may have a porous surface that is positioned adjacent bone, and a separate or opposite surface that has a generally impenetrable surface that is positioned adjacent soft tissue. Alternatively, the mesh material and/or mesh body may have one compartment that comprises a porous material, and a second compartment that comprises a substantially impenetrable material.

For either single and multi-compartment bone implants, the mesh material and/or mesh body may be closed after filling substances. Accordingly, the bone implant may be provided in an unfilled, unsealed state. After a substance for delivery is placed in the bone implant, the mesh material and/or mesh body of the bone implant may be permanently or temporarily closed. Temporary closure may be by tying, fold lock, cinching, or other means. A temporarily closed bone implant can be opened without damaging the mesh material and/or mesh body during surgical implantation to add or remove substances in the bone implant.

Suitable adhesives for use for closing the mesh material and/or mesh body of the bone implant may include, for example, cyanoacrylates (such as histoacryl, B Braun, which is n-butyl-2 cyanoacrylate, or Dermabond, which is 2-octylcyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; for example, in some circumstances, a temporary adhesive may be desirable, for example, for fixation during the surgical procedure and for a limited time thereafter while in other circumstances a permanent adhesive may be desired. Where the compartment is made of a material that is resorbable, the adhesive can be selected that would adhere for about as long as the material is present in the body.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms. In some embodiments, the bone implant may be attached to a tissue structure through a wrap, a suture, a wire, a string, an elastic band, a cable or a cable tie, or a combination thereof.

In other embodiments, suitable materials that form the mesh material and/or mesh body of the bone implant include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), polylactic acid-glycolic acid) (PLGA), polydioxanone, PVA, polyurethanes, polycarbonates, and others.

In various embodiments, the mesh material and/or mesh body comprises a polymer matrix. In some embodiments, DBM fibers and/or DBM powder are suspended in the polymer matrix to facilitate transfer of cells into and out of the mesh bag to induce bone growth at the surgical site. In other embodiments, the mesh material and/or mesh body further comprises mineralized bone fibers suspended in a polymer matrix. In some embodiments, the DRM powder is suspended in the polymer matrix between the DBM fibers and the mineralized bone fibers. In some embodiments, the DBM powder is suspended between the DBM fibers in the polymer matrix so as to reduce and/or eliminate gaps that exist between the fibers. In some embodiments, the DBM powder is suspended between the DBM fibers in the polymer matrix to improve osteoinductivity for facilitating bone fusion, for example, interspinous process fusion.

In some embodiments, the polymer matrix comprises a bioerodible, a bioabsorbable, and/or a biodegradable biopolymer that may provide immediate release or sustained release. Examples of suitable sustained release biopolymers include, but are not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), or combinations thereof. mPEG and/or PEG may be used as a plasticizer for PLGA, but other polymers/excipients may be used to achieve the same effect. mPEG imparts malleability to the polymer. In some embodiments, these biopolymers may also be coated on the mesh material and/or mesh body to provide a desired release profile or ingrowth of tissue. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the bone implant. In some embodiments, the range of the coating on the mesh material and/or mesh body ranges from about 5 microns to about 250 microns or 5 microns to about 200 microns.

In some embodiments, various components of the mesh material and/or mesh body comprise poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the mesh material and/or mesh body further comprises bone morphogenic proteins (BMPs), growth factors, antibiotics, angiogenesis promoting materials, bioactive agents or other actively releasing materials.

The mesh material and/or mesh body may be used to deliver a substance comprising any suitable biocompatible material. In specific embodiments, the mesh material and/or mesh body may be used to deliver surface demineralized bone chips, optionally of a predetermined particle size, fully demineralized bone fibers, optionally pressed, and/or allograft. For embodiments where the substance is a biologic, the substance may be autogenic, allogenic, xenogenic, or transgenic. Other suitable materials that may be positioned in the mesh material and/or mesh body include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, DBM, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above.

In accordance with some embodiments, the material to be positioned in the hollow compartment of the mesh material and/or mesh body may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; anti-microbials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, or the like; bioadhesives; bone morphogenetic proteins (BMPs including BMP-2); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

The material may have functional characteristics. Alternatively, other materials having functional characteristics may be incorporated into the mesh material and/or mesh body. Functional characteristics may include radiopacity, bacteriocidity, source for released materials tackiness, etc. Such characteristics may be imparted substantially throughout the mesh material and/or mesh body or at only certain positions or portions of the mesh material and/or mesh body.

Suitable radiopaque materials include, for example, ceramics, mineralized bone, ceramics/calcium phosphates/calcium sulfates, metal particles, fibers, and iodinated polymer (see, for example, WO/2007/143698). Polymeric materials may be used to form the mesh material and/or mesh body and be made radiopaque by iodinating them, such as taught for example in U.S. Pat. No. 6,585,755, herein incorporated by reference in its entirety. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

In some embodiments, the mesh material and/or mesh body may comprise a material that becomes tacky upon wetting. Such material may be, for example, a protein or gelatin based material. Tissue adhesives, including mussel adhesive proteins and cryanocrylates, may be used to impart tackiness to the mesh material and/or mesh body. In further examples, alginate or chitosan material may be used to impart tackiness to the mesh material and/or mesh body. In further embodiments, an adhesive substance or material may be placed on a portion of the mesh material and/or mesh body or in a particular region of the mesh material and/or mesh body to anchor that portion or region of the mesh material and/or mesh body in place at a surgical site, Methods A method of delivering a bone material to a surgical site is provided. The devices and bone material used in this method can be found in FIGS. 1-10. The method can be employed in a surgical treatment with a patient in a prone or supine position, and/or employ various surgical approaches to the spine, including anterior, posterior, posterior mid-line, direct lateral, and/or antero-lateral approaches, and in other body regions. The method may also be employed with procedures for treating the lumbar, cervical, thoracic, sacral and pelvic regions of a spinal column. The method may also be used on animals, bone models and other non-living substrates, such as, for example, in training, testing and demonstration.

Figure 10:
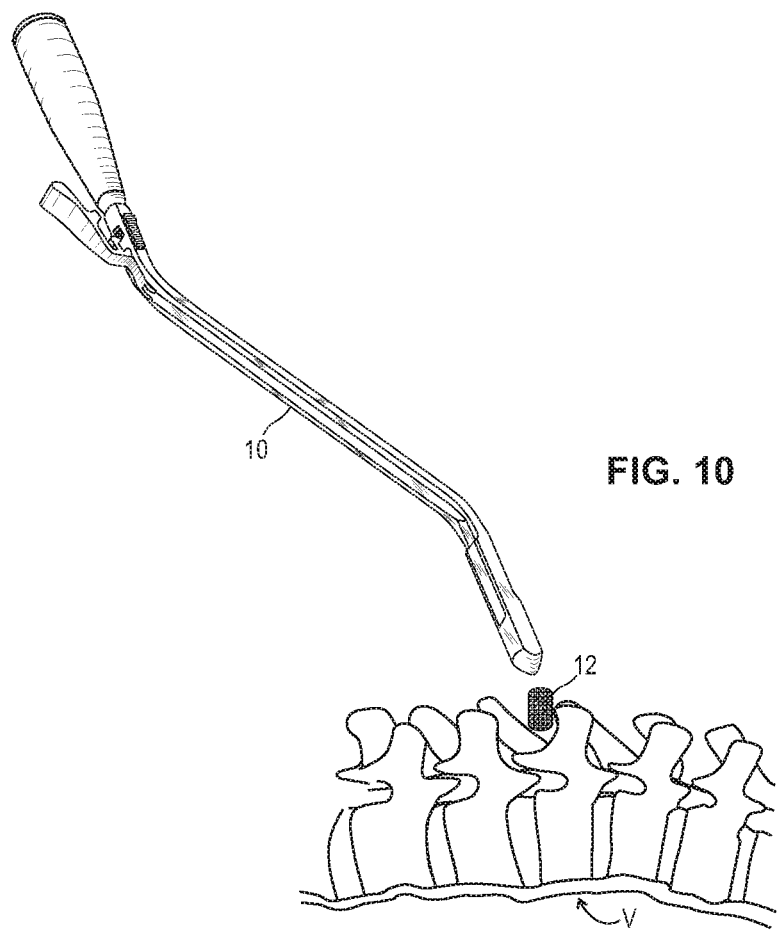
FIG. 10 is a front view of the device of FIG. 1 shown delivering a bone graft to vertebrae.

The method comprises providing a bone material delivery device 10 comprising a sleeve having an upper portion and a lower portion, the lower portion of the sleeve being substantially transverse to the upper portion and having a compartment for receiving a bone material, and an internal chamber disposed within the upper portion and the lower portion of the sleeve; and a plunger slidably disposed in at least the internal chamber of the sleeve, the plunger having a proximal end comprising a lever and a distal end comprising a plate; loading the compartment of the bone material delivery device with the bone material; and moving the plunger in a first position toward the lower portion of the sleeve to deliver the bone material 12 out of the lower portion of the sleeve and into the surgical site (e.g., vertebrae V as shown in FIG. 10).

The bone material may be used in a minimally invasive procedure via placement through a small incision, via delivery through the dilators, or other means. The size and shape may be designed with restrictions on delivery conditions. For example, the bone material may be percutaneously delivered to the surgical site, and in some cases, the surgical site is the posterior spine.

In some embodiments, the bone material may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others.

In some embodiments, the bone material is flexible enough so that it can be folded upon itself before it is implanted at, near, or in the surgical site.

Generally, the bone material may be applied to a pre-existing detect, to a created channel, or to a modified defect. Thus, for example, a channel may be formed in a bone, or a pre-existing defect may be cut to form a channel, for receipt of the bone material. The bone material may be configured to match the channel or defect. In some embodiments, the configuration of bone material may be chosen to match the channel. In other embodiments, the channel may be created, or the defect expanded or altered, to reflect a configuration of the bone material. The bone material may be placed in the defect or channel and, optionally, coupled using attachment mechanisms.

Although the invention has been described with reference to embodiments, persons skilled in the art will recognize that changes may be made in form and detail without departing from the spirit and scope of the invention.

What is claimed is:

1. A device for delivering a bone material to a surgical site, the device comprising: a body having an upper portion and a lower portion, the lower portion of the body being substantially transverse to the upper portion and having an opening for receiving a bone material; an internal chamber disposed within the upper portion and the lower portion; and a plunger slidably disposed in at least the internal chamber of the body, the plunger having a distal end configured for delivering the bone material out of the lower portion of the body, wherein movement of the plunger in a first position toward the lower portion of the body is configured to deliver the bone material from the lower portion of the body to the surgical site, wherein the body defines an opening that extends from the upper portion to the lower portion of the body for insertion of the plunger into the internal chamber.

2. The device according to claim 1, wherein the upper portion of the body comprises a handle.

3. The device according to claim 1, wherein the plunger comprises a proximal end opposite the distal end of the plunger, the proximal end comprising a lever and a spring that actuate movement of the plunger.

4. The device according to claim 3, wherein the distal end of the plunger comprises a link pivotably attached to a plate.

5. The device according to claim 4, wherein the plate is movable within the opening of the lower portion of the body.

6. The device according to claim 5, wherein the plate is configured for engagement with the bone material, and when the plunger is moved in the first position, the plate is pivoted by the link in a downward direction to eject the bone material from the plate, out of the opening of the lower portion of the body, and into the surgical site.

7. The device according to claim 1, wherein at least a section of the body and at least a section of the plunger are angled.

8. The device according to claim 1, wherein a proximal end of the plunger engages a spring, and the spring is encased in a housing that contacts an end of a lever casing such that when the housing is moved in a downward direction, the plunger is moved in the first position.

9. The device according to claim 8, wherein the lever casing is disposed on a proximal end of the upper portion of the body, and a lever locks and unlocks movement of the plunger.

10. The device according to claim 8, wherein the plunger comprises a plate, and the bone material is contained between the opening of the lower portion of the body and an upper surface of the plate, and when the plunger is moved in the first position, the bone material is ejected out of the opening of the lower portion of the body, and into the surgical site.

11. A device for delivering a bone material to a surgical site, the device comprising: a sleeve having an upper portion and a lower portion, the lower portion of the sleeve being substantially transverse to the upper portion and having a compartment for receiving a bone material, and an internal chamber disposed within the upper portion and the lower portion of the sleeve; and a plunger slidably disposed in at least the internal chamber of the sleeve, the plunger having a distal end comprising a plate configured for delivery of the bone material, wherein movement of the plunger in a first position toward the lower portion of the sleeve is configured to deliver the bone material out of the lower portion of the sleeve to the surgical site.

12. The device according to claim 11, wherein (i) the body defines an opening that extends from the upper portion to the lower portion of the body for insertion of the plunger into the internal chamber; or (ii) the upper portion of the sleeve comprises a handle.

13. The device according to claim 11, wherein the plunger comprises a proximal end opposite the distal end, the proximal end comprising a lever and a spring that actuate movement of the plunger.

14. The device according to claim 13, wherein the distal end of the plunger comprises a link pivotably attached to the plate, and the plate is movable within the compartment of the lower portion of the sleeve.

15. The device according to claim 14, wherein the plate is configured for engagement with the bone material, and when the plunger is moved in the first position, the plate is pivoted by the link in a downward direction to eject the bone material from the plate, out of the compartment of the lower portion of the sleeve, and into the surgical site.

16. The device according to claim 11, wherein a proximal end of the plunger engages a spring, and the spring is encased in a housing that contacts an end of a lever casing such that when the housing is moved in a downward direction, the plunger is moved in the first position; or (ii) a lever casing is disposed on a proximal end of the upper portion of the sleeve, and a lever locks and unlocks the housing.

17. The device according to claim 16, wherein the bone material is captured between the compartment of the lower portion of the sleeve and an upper surface of the plate, and when the plunger is moved in the first position, the bone material is ejected out of the compartment of the lower portion of the sleeve, and into the surgical site.

18. A method of delivering a bone material to a surgical site, the method comprising: providing a bone material delivery device comprising a sleeve having an upper portion and a lower portion, the lower portion of the sleeve being substantially transverse to the upper portion and having a compartment for receiving a bone material, and an internal chamber disposed within the upper portion and the lower portion of the sleeve; and a plunger slidably disposed in at least the internal chamber of the sleeve, the plunger having a proximal end comprising a lever and a distal end comprising a plate; loading the compartment of the bone material delivery device with the bone material; and moving the plunger in a first position toward the lower portion of the sleeve to deliver the bone material out of the lower portion of the sleeve and into the surgical site.

19. The method of claim 18, wherein (i) the bone material is percutaneously delivered to the surgical site; or (ii) the surgical site is a posterior spine.

* * * * *